(12) United States Patent
Kubota

(10) Patent No.: US 7,829,206 B2
(45) Date of Patent: Nov. 9, 2010

(54) BENZANTHRACENE DERIVATIVE AND ELECTROLUMINESCENCE DEVICE USING THE SAME

(75) Inventor: Mineyuki Kubota, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 643 days.

(21) Appl. No.: 11/695,219

(22) Filed: Apr. 2, 2007

(65) Prior Publication Data

US 2007/0273272 A1 Nov. 29, 2007

(30) Foreign Application Priority Data

Apr. 3, 2006 (JP) .............................. 2006-102339

(51) Int. Cl.
*H01L 51/54* (2006.01)

(52) U.S. Cl. ...................... 428/690; 428/917; 313/504; 313/506

(58) Field of Classification Search ........................ None
See application file for complete search history.

(56) References Cited

U.S. PATENT DOCUMENTS

| 6,696,178 B2 * | 2/2004 | Igarashi ..................... 428/690 |
| 2004/0247937 A1 * | 12/2004 | Chen et al. .................. 428/690 |

FOREIGN PATENT DOCUMENTS

| JP | 61-44975 | 3/1986 |
| JP | 3-200889 | 9/1991 |
| JP | 7-138561 | 5/1995 |
| JP | 8-239655 | 9/1996 |
| JP | 2000-178548 | 6/2000 |
| JP | 2005-263721 | 9/2005 |
| WO | WO 2004020387 | * 3/2004 |
| WO | WO 2005/090365 A1 | 9/2005 |

OTHER PUBLICATIONS

S. D. Saraf, et al., "The Use of Mixed Grignard Reagents in the Double Bradsher Reaction," International Journal of Methods in Synthetic Organic Chemistry, No. 12, Dec. 1970, p. 655 with 1 cover page.

Frank A. Vingiello, et al., "An Unusual Elbs-type Reaction Observed during a Study of the Cyclization of Ketones," Journal of the American Chemical Society, vol. 80, Apr. 5, 1958, pp. 1714-1716.

C. W. Tang, et al., "Organic electroluminescent diodes," Applied Physics Letters, vol. 51, No. 12, Sep. 21, 1987, pp. 913-915.

* cited by examiner

*Primary Examiner*—Dawn Garrett
(74) *Attorney, Agent, or Firm*—Oblon, Spivak, McClelland, Maier & Neustadt, L.L.P.

(57) ABSTRACT

A benzanthracene derivative having hydrogen atom at the 12-position, and an organic electroluminescence device having an organic thin film layer, which has one layer or a plurality of layers including at least a light emitting layer, is disposed between a cathode and an anode and contains the benzanthracene derivative in at least one layer in the organic thin film layer singly or as a component of a mixture. The electroluminescence device provides a great efficiency of light emission, has a long life and exhibits an excellent chromaticity.

9 Claims, No Drawings

BENZANTHRACENE DERIVATIVE AND ELECTROLUMINESCENCE DEVICE USING THE SAME

TECHNICAL FIELD

The present invention relates to a benzanthracene derivative having hydrogen atom at the 12-position and an organic electro-luminescence (referred to as EL, hereinafter) device using the derivative. More particularly, the present invention relates to a benzanthracene derivative having hydrogen atom at the 12-position and an organic EL device exhibiting an improved chromaticity of emitted light by using the derivative.

BACKGROUND ART

An organic EL device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used tris(8-hydroxyquinolinolato)aluminum for the light emitting layer and a triphenyldiamine derivative for the hole transporting layer. Advantages of the laminate structure are that the efficiency of hole injection into the light emitting layer can be increased, that the efficiency of forming excitons which are formed by blocking and recombining electrons injected from the cathode can be increased, and that excitons formed within the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material, chelate complexes such as tris(8-quinolinolato)aluminum, coumarine derivatives, tetraphenyl-butadiene derivatives, bisstyrylarylene derivatives and oxadiazole derivatives are known. It is reported that light in the visible region ranging from blue light to red light can be obtained by using these light emitting materials, and development of a device exhibiting color images is expected (for example, Patent Reference 1, Patent Reference 2 and Patent Reference 3).

As the light emitting material, a benzanthracene derivative having an aromatic hydrocarbon ring at the 12-position is disclosed in Patent Reference 4. The benzanthracene derivative is used as the light emitting material emitting blue light. However, the benzanthracene derivative has drawbacks in that the obtained device does not have a sufficient life and does not exhibit excellent chromaticity.

[Patent Reference 1] Japanese Patent Application Laid-Open No. Heisei 8 (1996)-239655

[Patent Reference 2] Japanese Patent Application Laid-Open No. Heisei 7 (1995)-138561

[Patent Reference 3] Japanese Patent Application Laid-Open No. Heisei 3 (1991)-200889

[Patent Reference 4] Japanese Patent Application Laid-Open No. 2000-178548

DISCLOSURE OF THE INVENTION

Problems to be Overcome by the Invention

The present invention has been made to overcome the above problem and has an object of providing an organic EL device exhibiting an excellent chromaticity and a benzanthracene derivative having hydrogen atom at the 12-position which is advantageously used as the light emitting material in the organic EL device of the present invention.

Means for Overcoming the Problems

As the result of intensive studies by the present inventors to achieve the above object, it was found that an organic EL device providing a great efficiency of light emission, having a long life and exhibiting an excellent chromaticity could be prepared by using a benzanthracene derivative having hydrogen atom at the 12-position which is represented by one of the following general formulae (1) to (4) as the light emitting material. The present invention has been completed based on the knowledge.

The present invention provides a benzanthracene derivative having hydrogen atom at a 12-position which is represented by following general formula (1):

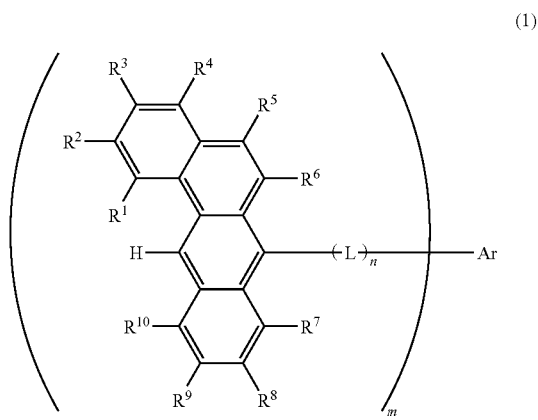

(1)

wherein $R^1$ to $R^{10}$ each independently represent hydrogen atom, a substituted or unsubstituted aromatic hydrocarbon cyclic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted cycloalkyl group having 3 to 50 nuclear carbon atoms, a substituted or unsubstituted alkoxy group having 1 to 50 carbon atoms, a substituted or unsubstituted aralkyl group having 6 to 50 nuclear carbon atoms, a substituted or unsubstituted aryloxy group having 5 to 50 nuclear carbon atoms, a substituted or unsubstituted arylthio group having 5 to 50 nuclear carbon atoms, a substituted or unsubstituted alkoxycarbonyl group having 1 to 50 carbon atoms, a substituted or unsubstituted silyl group 1 to 50 carbon atoms, carboxy group, a halogen atom, cyano group, nitro group or hydroxy group;

L represents a linking group, which is a single bond, a substituted or unsubstituted divalent aromatic hydrocarbon cyclic group having 6 to 50 nuclear carbon atoms, a substituted or unsubstituted divalent aromatic heterocyclic group having 5 to 50 nuclear atoms, a substituted or unsubstituted fluorenylene group or a substituted or unsubstituted carbazolylene group;

n represents an integer of 1 to 4 and, when n represents an integer of 2 or greater, a plurality of linking groups represented by L may be same with or different from each other;

Ar represents a single bond, hydrogen atom, a substituted or unsubstituted aromatic hydrocarbon cyclic group having 6 to 50 nuclear carbon atoms, a substituted or unsubstituted aromatic heterocyclic group having 5 to 50 nuclear atoms, fluorenyl group or carbazolyl group; and m represents an integer of 1 to 4 and, when m represents an integer of 2 or greater, a plurality of atoms and groups represented by $R^1$ to $R^{10}$ and L may be same with or different from each other.

The present invention also provides an organic electroluminescence device comprising a cathode, an anode and an organic thin film layer which comprises one layer or a plurality of layers comprising at least a light emitting layer and is disposed between the cathode and the anode, wherein the organic thin film layer comprises the benzanthracene derivatives having hydrogen atom at a 12-position described above singly or as a component of a mixture.

The Effect of the Invention

Using the benzanthracene derivative having hydrogen atom at the 12-position of the present invention, an organic EL device providing a great efficiency of light emission, having a long life and exhibiting an excellent chromaticity can be prepared.

THE MOST PREFERRED EMBODIMENT TO CARRY OUT THE INVENTION

The benzanthracene derivative having hydrogen atom at the 12-position of the present invention is represented by the following general formula (1):

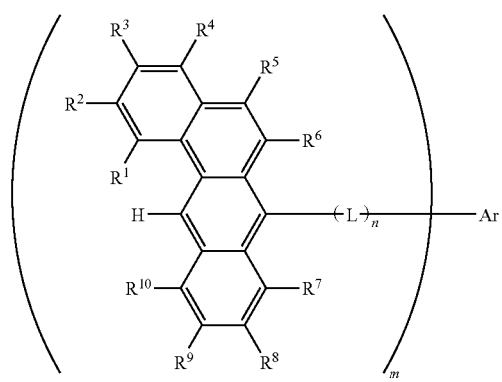

(1)

In general formula (1), $R^1$ to $R^{10}$ each independently represent hydrogen atom, a substituted or unsubstituted aromatic hydrocarbon cyclic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted cycloalkyl group having 3 to 50 nuclear carbon atoms, a substituted or unsubstituted alkoxy group having 1 to 50 carbon atoms, a substituted or unsubstituted aralkyl group having 6 to 50 nuclear carbon atoms, a substituted or unsubstituted aryloxy group having 5 to 50 nuclear carbon atoms, a substituted or unsubstituted arylthio group having 5 to 50 nuclear carbon atoms, a substituted or unsubstituted alkoxycarbonyl group having 1 to 50 carbon atoms, a substituted or unsubstituted silyl group 1 to 50 carbon atoms, carboxy group, a halogen atom, cyano group, nitro group or hydroxy group.

L represents a linking group, which is the single bond, a substituted or unsubstituted divalent aromatic hydrocarbon cyclic group having 6 to 50 nuclear carbon atoms, a substituted or unsubstituted divalent aromatic heterocyclic group having 5 to 50 nuclear atoms, a substituted or unsubstituted fluorenylene group or a substituted or unsubstituted carbazolylene group.

n represents an integer of 1 to 4. When n represents an integer of 2 or greater, a plurality of linking groups represented by L may be the same with or different from each other.

Ar represents the single bond, hydrogen atom, a substituted or unsubstituted aromatic hydrocarbon cyclic group having 6 to 50 nuclear carbon atoms, a substituted or unsubstituted aromatic heterocyclic group having 5 to 50 nuclear atoms, fluorenyl group or carbazolyl group.

m represents an integer of 1 to 4 and preferably 1 to 3. When m represents an integer of 2 or greater, a plurality of atoms and groups represented by $R^1$ to $R^{10}$ and L may be the same with or different from each other.

It is preferable that the benzanthracene derivative having hydrogen atom at the 12-position which is represented by general formula (1) is a compound represented by the following general formula (2):

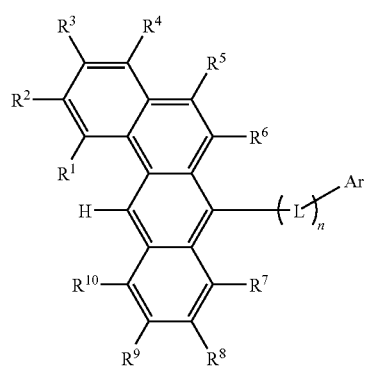

(2)

In general formula (2), $R^1$ to $R^{10}$, L and n are each independently same as defined in general formula (1), and Ar represents hydrogen atom, a substituted or unsubstituted aromatic hydrocarbon cyclic group having 6 to 50 nuclear carbon atoms, a substituted or unsubstituted aromatic heterocyclic group having 5 to 50 nuclear atoms, fluorenyl group or carbazolyl group.

It is preferable that the benzanthracene derivative having hydrogen atom at the 12-position which is represented by general formula (1) is a compound represented by the following general formula (3):

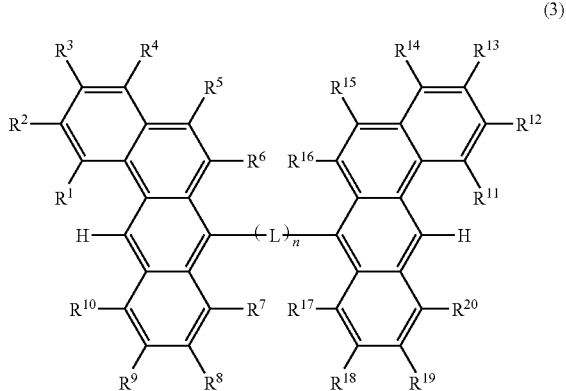

(3)

In general formula (3), $R^1$ to $R^{20}$ are each independently same as defined for $R^1$ to $R^{10}$ in general formula (1), and L and n are each independently same as defined in general formula (1).

It is preferable that the benzanthracene derivative having hydrogen atom at the 12-position which is represented by general formula (1) is a compound represented by the following general formula (4):

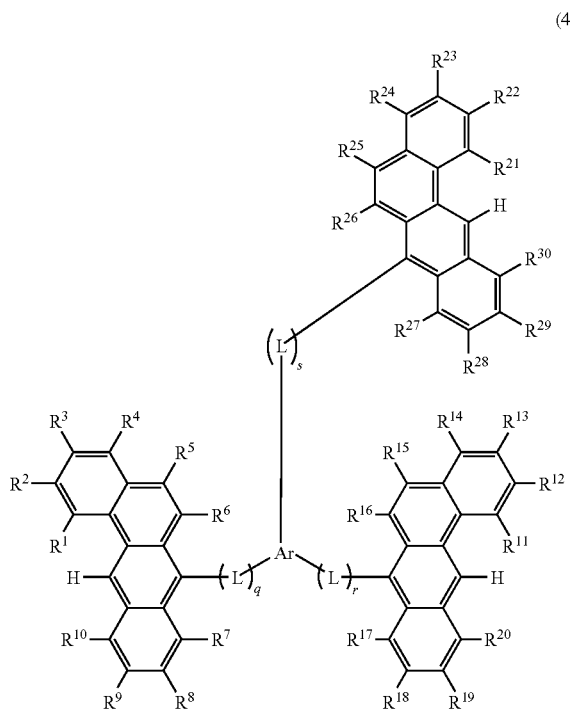

(4)

In general formula (4), $R^1$ to $R^{30}$ are each independently same as defined for $R^1$ to $R^{10}$ in general formula (1), L is same as defined in general formula (1), q, r and s are each same as defined for n in general formula (1), and Ar represents a substituted or unsubstituted aromatic hydrocarbon cyclic group having 6 to 50 nuclear carbon atoms, a substituted or unsubstituted aromatic heterocyclic group having 5 to 50 nuclear atoms, fluorenyl group or carbazolyl group.

Examples of the substituted and unsubstituted aromatic hydrocarbon cyclic groups represented by $R^1$ and $R^{30}$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4"-t-butyl-p-terphenylyl group.

Among these groups, phenyl group, 1-naphthyl group, 2-naphthyl group, 9-(10-phenyl)anthryl group, 9-(10-naphthyl-1-yl)anthryl group, 9-(10-naphthyl-2-yl)anthryl group, 9-phenanthryl group, 1-pyrenyl group, 2-pyrenyl group, 4-pyrenyl group, 2-biphenylyl group, 3-biphenylyl group, 4-biphenylyl group, o-tolyl group, m-tolyl group, p-tolyl group and p-t-butylphenyl group are preferable.

Examples of the substituted and unsubstituted aromatic heterocyclic groups represented by $R^1$ to $R^{30}$ include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10- yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methyl-pyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Examples of the substituted and unsubstituted alkyl groups represented by $R^1$ to $R^{30}$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloro-isobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyano-methyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group.

Examples of the substituted and unsubstituted cycloalkyl groups represented by $R^1$ to $R^{30}$ include cyclopropyl group, cyclobutyl group, cyclopentyl group, cyclohexyl group, 4-methylcyclohexyl group, 1-adamantyl group, 2-adamantyl group, 1-norbornyl group and 2-norbornyl group.

The alkoxy group represented by $R^1$ to $R^{30}$ is a group represented by —OY. Examples of the group represented by Y include the groups described as the examples of the alkyl group.

Examples of the substituted and unsubstituted aralkyl groups represented by $R^1$ to $R^{30}$ include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthyl-isopropyl group, β-naphthylmethyl group, 1-β-naphthylethyl group, 2-β-naphthylethyl group, 1-β-naphthylisopropyl group, 2-β-naphthyl-isopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The substituted and unsubstituted aryloxy groups represented by $R^1$ to $R^{30}$ are represented by —OY'. Examples of the group represented by Y' include the groups described as the examples of the aryl group and the aromatic heterocyclic group.

The substituted and unsubstituted arylthio groups represented by $R^1$ to $R^{30}$ are represented by —SY'. Examples of the group represented by Y' include the groups described above as the examples of the group represented by Y' in the aryloxy group.

The substituted and unsubstituted alkoxycarbonyl groups represented by $R^1$ to $R^{30}$ are represented by —COOZ. Examples of the group represented by Z include the groups described above as the examples of the alkyl group.

Examples of the substituted and unsubstituted silyl groups represented by $R^1$ to $R^{30}$ include trimethylsilyl group, triethylsilyl group, t-butyldimethylsilyl group, vinyldimethylsilyl group, propyldimethylsilyl group and triphenylsilyl group, which may be substituted.

Examples of the halogen atom represented by $R^1$ to $R^{30}$ include fluorine atom, chlorine atom, bromine atom and iodine atom.

In general formulae (1) to (4), L represents a linking group, which is a single bond, a substituted or unsubstituted divalent aromatic hydrocarbon cyclic group having 6 to 50 nuclear carbon atoms, a substituted or unsubstituted divalent aromatic heterocyclic group having 5 to 50 nuclear carbon atoms, a substituted or unsubstituted fluorenylene group or a substituted or unsubstituted carbazolylene group.

Examples of the substituted and unsubstituted divalent aromatic hydrocarbon cyclic groups having 6 to 50 nuclear carbon atoms represented by L include divalent groups obtained by removing one hydrogen atom from the aromatic hydrocarbon groups represented by $R^1$ to $R^{30}$ described above. Divalent groups derived from benzene, naphthalene, anthracene, phenanthrene, naphthacene, chrysene and pyrene are preferable.

Examples of the substituted and unsubstituted divalent aromatic heterocyclic residue groups having 5 to 50 nuclear atoms represented by L include divalent groups obtained by removing one hydrogen atom from the aromatic heterocyclic groups represented by $R^1$ to $R^{30}$ described above. Divalent groups derived from pyrrol, pyridine, indole, isoindole, quinoline, carbazole, phenanthroline, thiophene, furan, benzothiophene, benzofuran, benzimidazole, dibenzothiophene and dibenzofuran are preferable.

n represents an integer of 1 to 4. When n represents an integer of 2 or greater, a plurality of group represented by L may be the same with or different from each other.

In general formal (1), Ar represents a single bond, hydrogen atom, a substituted or unsubstituted aromatic hydrocarbon cyclic group, a substituted or unsubstituted aromatic heterocyclic group, fluorenyl group or carbazolyl group. In general formula (2), Ar represents hydrogen atom, a substituted or unsubstituted aromatic hydrocarbon cyclic group, a substituted or unsubstituted aromatic heterocyclic group, fluorenyl group or carbazolyl group. In general formula (4), Ar represents a substituted or unsubstituted aromatic hydrocarbon cyclic group, a substituted or unsubstituted aromatic heterocyclic group, fluorenyl group or carbazolyl group.

Examples of the substituted and unsubstituted divalent aromatic hydrocarbon cyclic residue groups represented by Ar include divalent groups obtained by removing one hydrogen atom from aromatic hydrocarbon groups represented by $R^1$ to $R^{30}$ described above similarly to the groups described as the examples of the groups represented by L. Preferable examples include the groups described above as the preferable examples of the groups represented by L.

Examples of the substituted and unsubstituted divalent aromatic heterocyclic residue groups represented by Ar include divalent groups obtained by removing one hydrogen atom from aromatic heterocyclic groups represented by $R^1$ to $R^{30}$ described above similarly to the groups described as the examples of the groups represented by L. Preferable examples include the groups described above as the preferable examples of the groups represented by L.

m represents an integer of 1 to 4 and preferably 1 to 3. When m represents an integer of 2 or greater, a plurality of atoms and groups represented by $R^1$ to $R^{30}$ and L may be the same with or different from each other.

Examples of the substituent to the group represented by $R^1$ to $R^{30}$ and Ar include alkyl groups (such as methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyano-methyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitro methyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group and 2-norbornyl group), alkoxy groups having 1 to 6 carbon atoms (such as ethoxy group, methoxy group, isopropoxy group, n-propoxy group, s-butoxy group, t-butoxy group, pentoxy group, hexyloxy group, cyclopentoxy group and cyclohexyloxy group), aryl groups having 5 to 40 nuclear atoms, amino groups substituted with aryl groups having 5 to 40 nuclear atoms, ester groups having aryl groups having 5 to 40 nuclear atoms, ester groups having alkyl groups having 1 to 6 carbon atoms, cyano group, nitro group and halogen atoms.

Specific examples of the benzanthracene derivatives represented by general formula (1) of the present invention are shown in the following. However, the benzanthracene derivative of the present invention is not limited to these compounds.

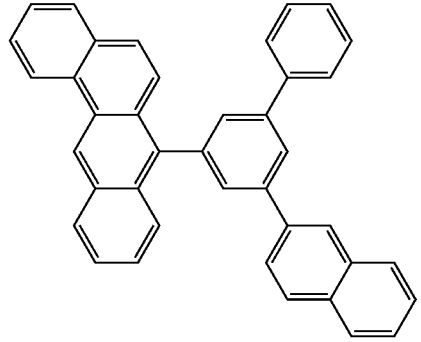

BAN-1

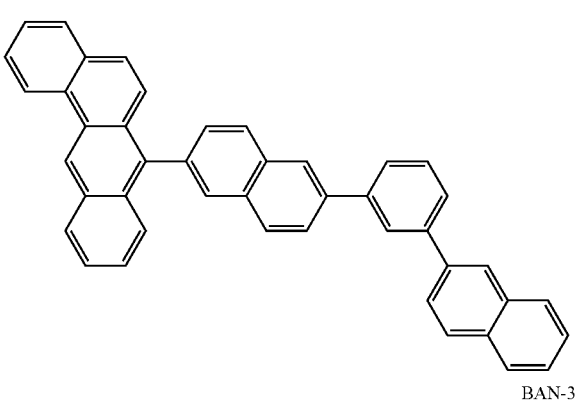

BAN-2

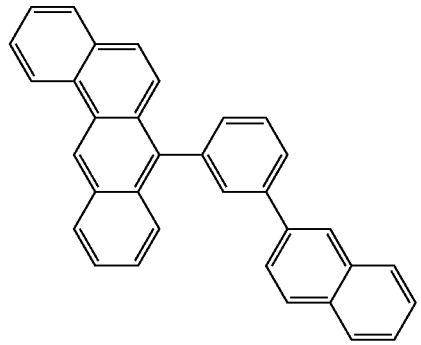

BAN-3

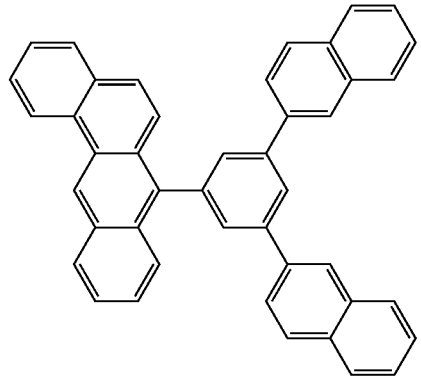

BAN-4

-continued
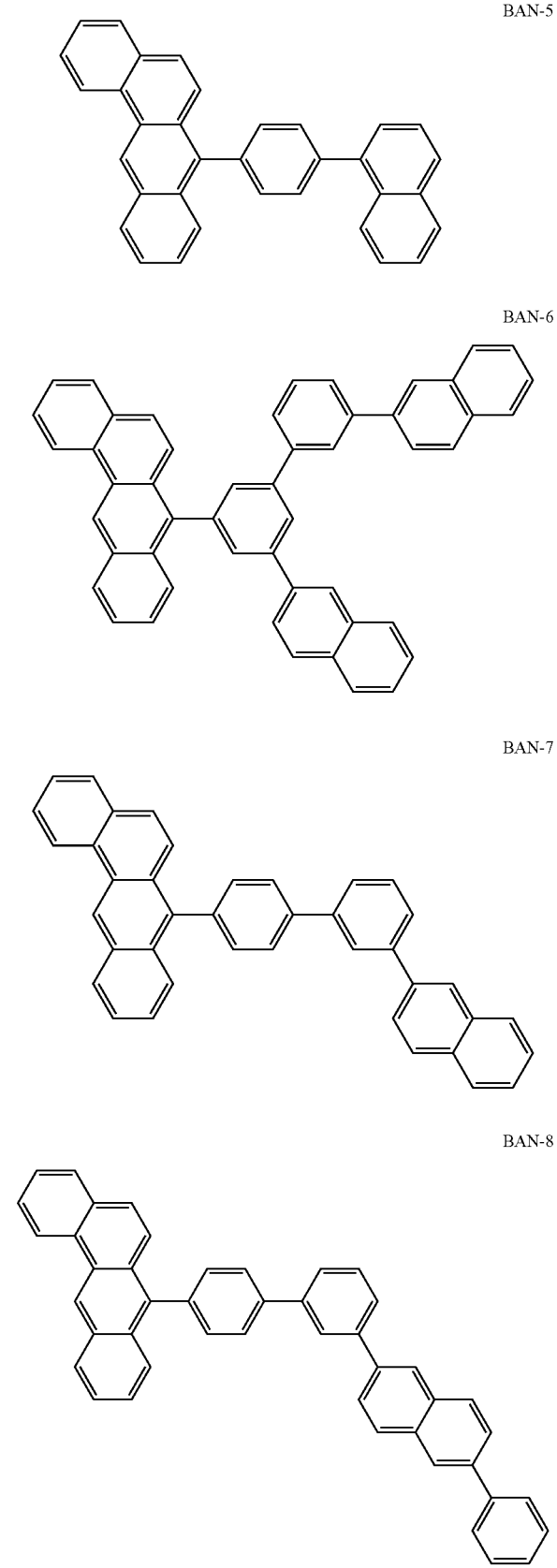
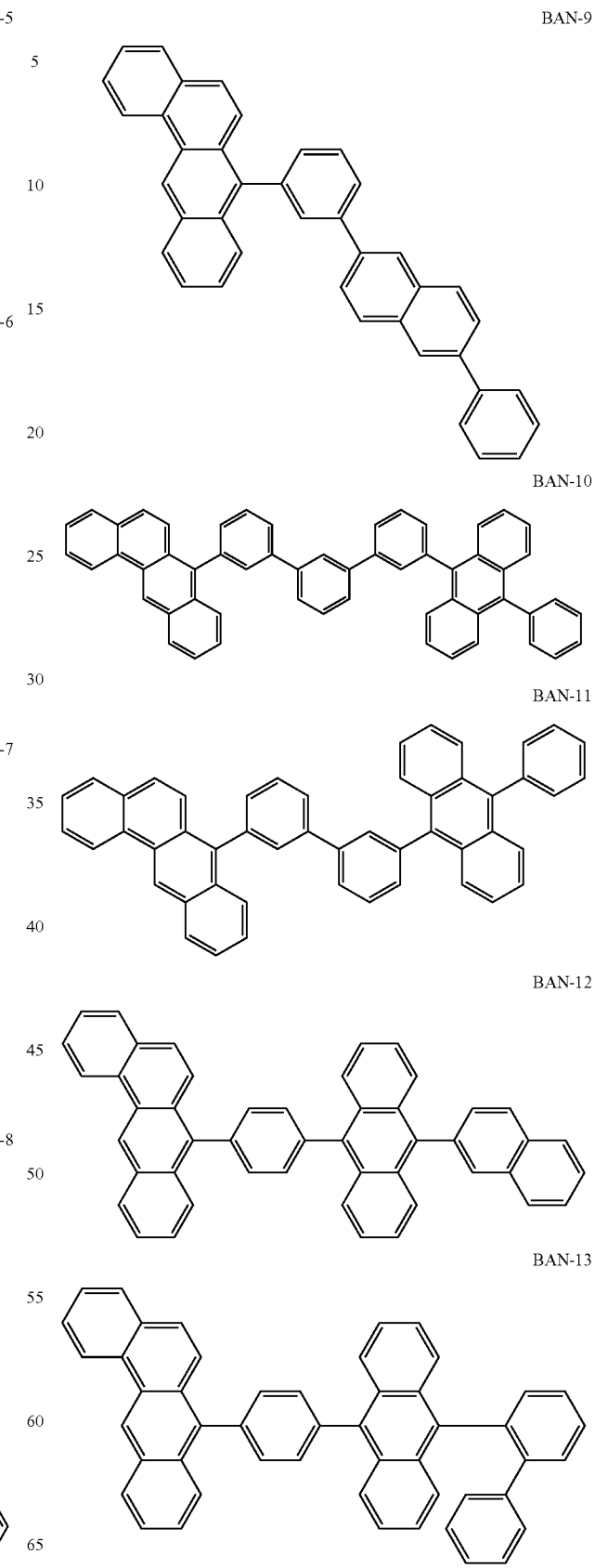

-continued
BAN-14
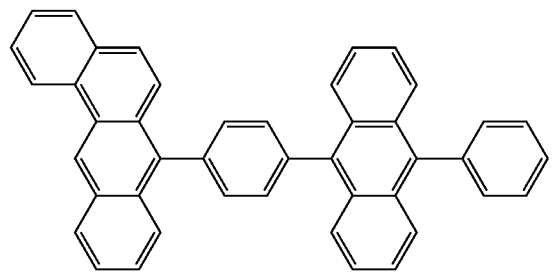
BAN-15
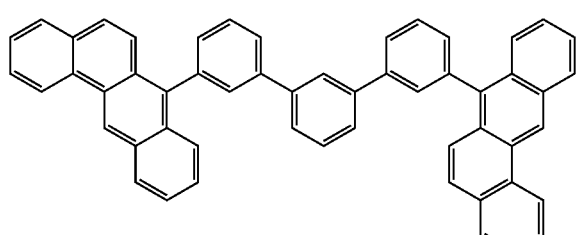
BAN-16
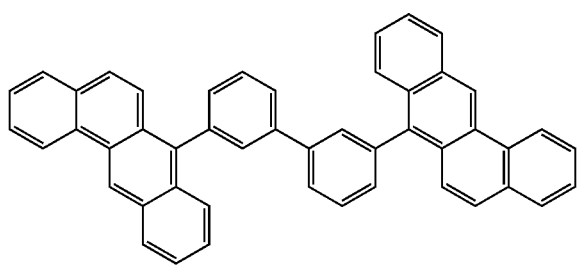
BAN-17
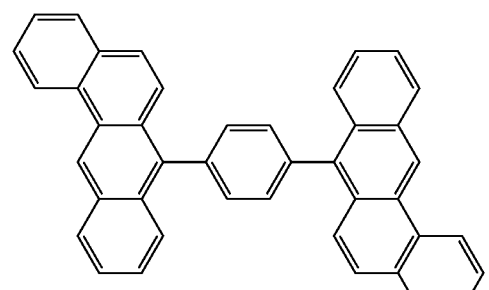
BAN-18
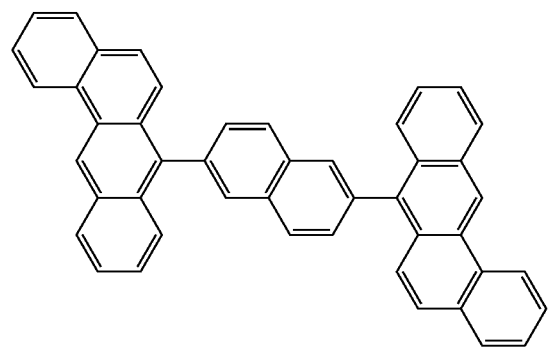
-continued
BAN-19
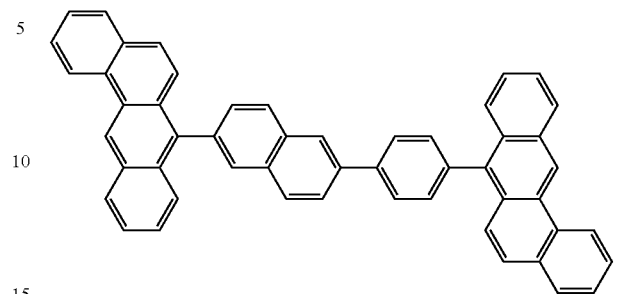
BAN-20
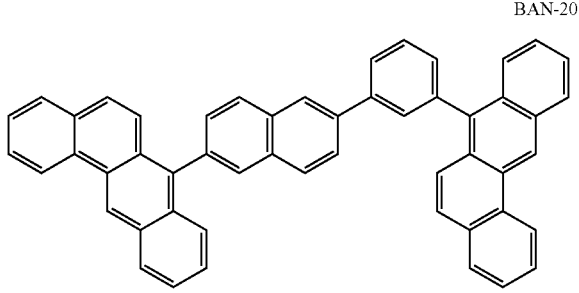
BAN-21
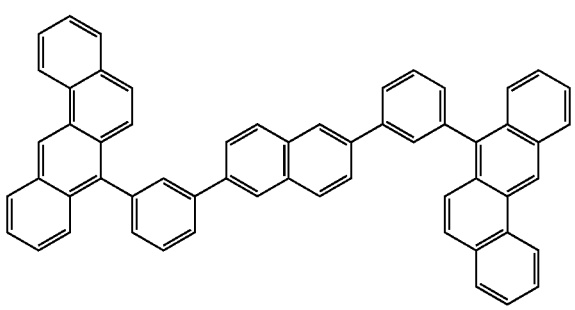
BAN-22
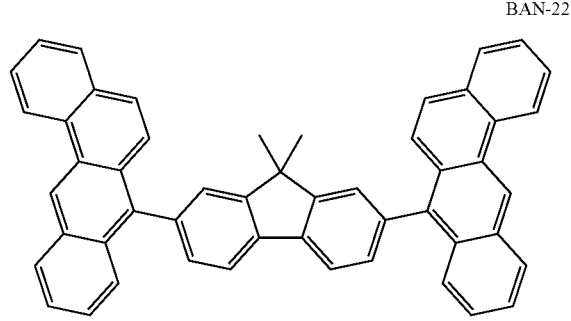
BAN-23
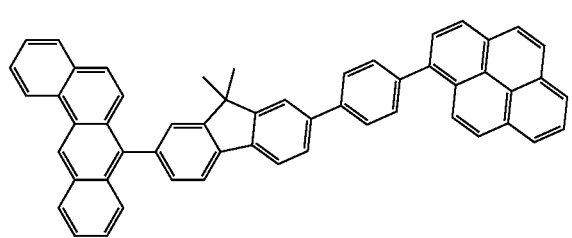

BAN-24
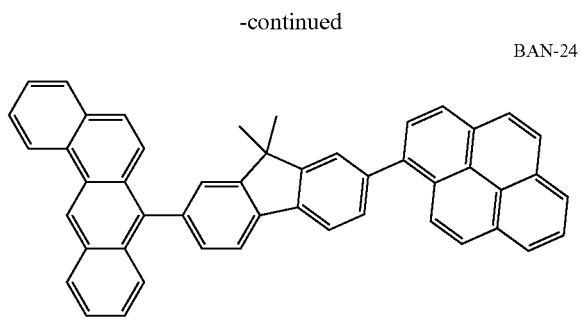
BAN-27
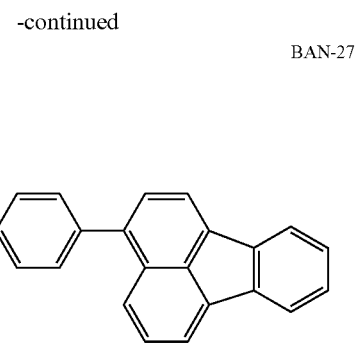
BAN-25
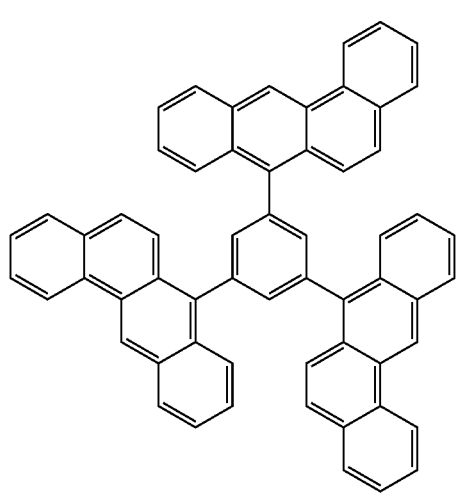
BAN-28
BAN-29
BAN-26
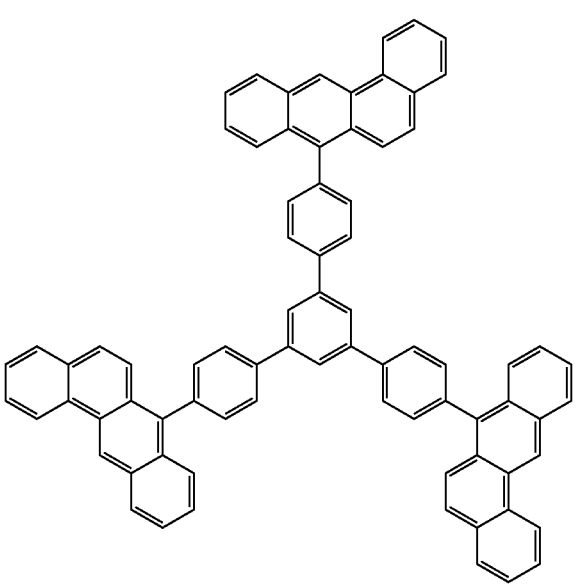
BAN-30
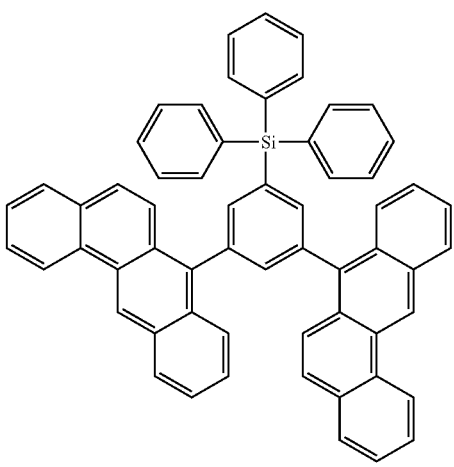

-continued

BAN-31
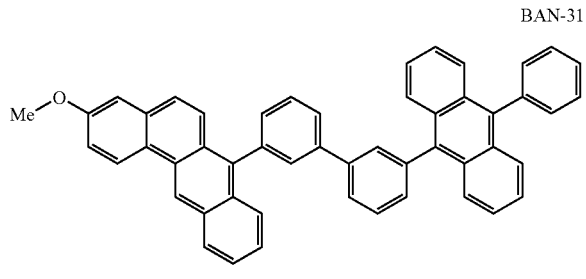

BAN-32
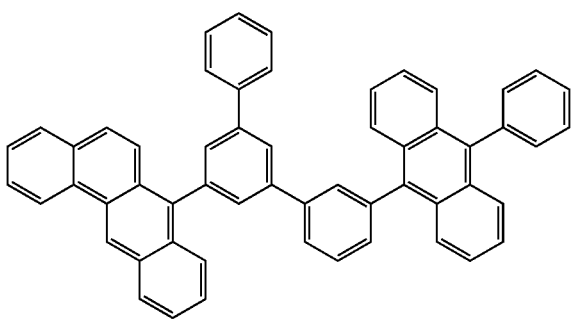

BAN-33
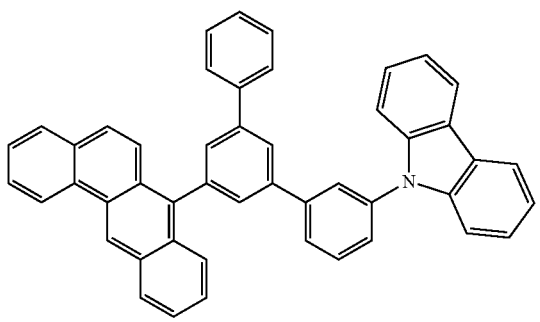

BAN-34
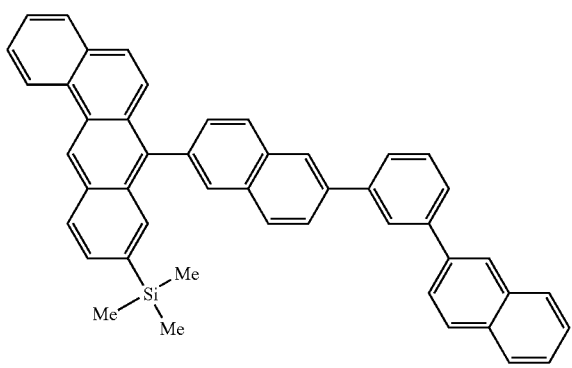

-continued

BAN-35

BAN-36

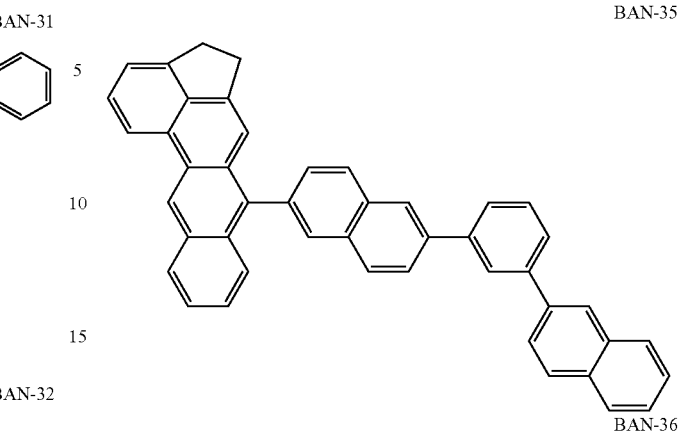

It is preferable that the benzanthracene derivative of the present invention having hydrogen atom at the 12-position is used as the light emitting material for organic EL devices and more preferably as the host material for organic EL devices.

The organic EL device of the present invention comprises a cathode, an anode and an organic thin film layer which comprises one layer or a plurality of layers comprising at least a light emitting layer and is disposed between the cathode and the anode, wherein the organic thin film layer comprises at least one compound selected from benzanthracene derivatives having hydrogen atom at the 12-position which are represented by general formula (1) described above singly or as a component of a mixture.

In the organic EL device of the present invention, it is preferable that the light emitting layer further comprises an arylamine compound and/or a styrylamine compound.

As the styrylamine compound, compounds represented by the following general formula (A) are preferable:

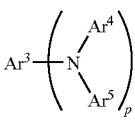
(A)

wherein $Ar^3$ represents a group selected from phenyl group, biphenyl group, terphenyl group, stilbene group and distyrylaryl groups, $Ar^4$ and $Ar^5$ each represent hydrogen atom or an aromatic hydrocarbon group having 6 to 20 carbon atoms, the groups represented by $Ar^3$, $Ar^4$ and $Ar^5$ may be substituted, p represents an integer of 1 to 4, it is preferable that at least one of the groups represented by $Ar^4$ and $Ar^5$ is substituted with styryl group, and at least one of the groups represented by $Ar^3$ to $Ar^5$ has a substituted or unsubstituted styryl group.

Examples of the aromatic hydrocarbon group having 6 to 20 carbon atoms include phenyl group, naphthyl group, anthranyl group, phenanthryl group and terphenyl group.

As the arylamine compound, compounds represented by the following general formula (B) are preferable:

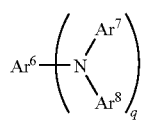
(B)

wherein $Ar^6$ to $Ar^8$ each represent a substituted or unsubstituted aryl group having 5 to 40 nuclear carbon atoms, and q represents an integer of 1 to 4.

Examples of the aryl group having 5 to 40 nuclear carbon atoms include phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group, acenaphthofluoranthenyl group, stilbene group, perylenyl group, chrysenyl group, pycenyl group, triphenylenyl group, rubicenyl group, benzanthracenyl group, phenylanthranyl group, bisanthracenyl group and aryl groups represented by the following general formula (C) or expressed by the following formula (D). Among these groups, naphthyl group, anthranyl group, chrysenyl group, pyrenyl group and the aryl group expressed by formula (D) are preferable.

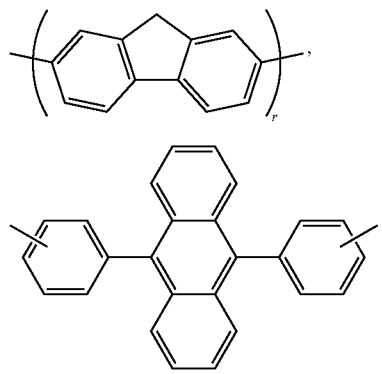

In general formula (C), r represents an integer of 1 to 3.

Preferable examples of the substituent to the aryl group described above include alkyl groups having 1 to 6 carbon atoms such as ethyl group, methyl group, isopropyl group, n-propyl group, s-butyl group, t-butyl group, pentyl group, hexyl group, cyclopentyl group and cyclohexyl group; alkoxy groups having 1 to 6 carbon atoms such as ethoxy group, methoxy group, isopropoxy group, n-propoxy group, s-butoxy group, t-butoxy group, pentoxy group, hexyloxy group, cyclopentoxy group and cyclohexyloxy group; aryl groups having 5 to 40 nuclear carbon atoms; amino groups substituted with an aryl group having 5 to 40 nuclear carbon atoms; ester groups having an aryl group having 5 to 40 nuclear carbon atoms; ester groups having an alkyl group having 1 to 6 carbon atoms; cyano group; nitro group; and halogen atoms.

The construction of the organic EL device of the present invention will be described in the following.

Typical examples of the construction of the organic EL device include:

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;
(9) An anode/an insulating layer/a light emitting layer/an insulating layer/a cathode;
(10) An anode/an inorganic semiconductor layer/an insulating layer/a light emitting layer/an insulating layer/a cathode;
(11) An anode/an organic semiconductor layer/an insulating layer/a light emitting layer/an insulating layer/a cathode;
(12) An anode/an insulating layer/a hole injecting layer/a hole transporting layer/a light emitting layer/an insulating layer/a cathode; and
(13) An anode/an insulating layer/a hole injecting layer/a hole transporting layer/a light emitting layer/an electron injecting layer/a cathode.

Among the above constructions, construction (8) is preferable. However, the construction of the organic EL device is not limited to those shown above as the examples.

In the organic EL device of the present invention, it is preferable that the light emitting zone or the hole transporting zone among the constituting elements of the device comprises the benzanthracene derivative having hydrogen atom at the 12-position of the present invention although any of the organic layers may comprise the benzanthracene derivative. The content of the benzanthracene derivative is selected in the range of 30 to 100% by mole.

The organic EL device is, in general, prepared on a substrate transmitting light. The substrate transmitting light is the substrate supporting the organic EL device. It is preferable that the substrate transmitting light has a transmittance of light of 50% or greater in the visible region of 400 to 700 nm. It is also preferable that a flat and smooth substrate is used.

As the substrate transmitting light, for example, glass plates and synthetic resin plates are advantageously used. Examples of the glass plate include plates made of soda-lime glass, glass containing barium and strontium, lead glass, aluminosilicate glass, borosilicate glass, barium borosilicate glass and quartz. Examples of the synthetic resin plate include plates made of polycarbonate resins, acrylic resins, polyethylene terephthalate resins, polyether sulfide resins and polysulfone resins.

The anode has the function of injecting holes into the hole transporting layer or the light emitting layer. It is effective that the anode has a work function of 4.5 eV or greater. Examples of the material for the anode used in the present invention include indium tin oxide alloys (ITO), tin oxide (NESA), gold, silver, platinum and copper. For the cathode, materials having a small work function are preferable for the purpose of injecting electrons into the electron transporting layer or the light emitting layer.

The anode can be prepared by forming a thin film of the electrode substance described above in accordance with a process such as the vapor deposition process and the sputtering process.

When the light emitted from the light emitting layer is obtained through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of 10 nm to 1 μm and preferably in the range of 10 to 200 nm although the range may be different depending on the used material.

The light emitting layer in the organic EL device of the present invention has the following functions:

(i) The injecting function: the function of injecting holes from the anode or the hole injecting layer and injecting electrons from the cathode or the electron injecting layer when an electric field is applied;
(ii) The transporting function: the function of transporting injected charges (electrons and holes) by the force of the electric field; and
(iii) The light emitting function: the function of providing the field for recombination of electrons and holes and leading the recombination to the emission of light.

As the process for forming the light emitting layer, a conventional process such as the vapor deposition process, the spin coating process and the LB process can be used. It is particularly preferable that the light emitting layer is a molecular deposit film. The molecular deposit film is a thin film formed by deposition of a material compound in the gas phase or a thin film formed by solidification of a material compound in a solution or in the liquid phase. In general, the molecular deposit film can be distinguished from the thin film formed in accordance with the LB process (the molecular accumulation film) based on the differences in aggregation structures and higher order structures and the functional differences caused by these structural differences.

As disclosed in Japanese Patent Application Laid-Open No. Showa 57 (1982)-51781, the light emitting layer can also be formed by dissolving a binder such as a resin and the material compounds into a solvent to prepare a solution, followed by forming a thin film from the prepared solution in accordance with the spin coating process or the like.

In the present invention, where desired, the light emitting layer may comprise conventional light emitting materials other than the light emitting material comprising the benzanthracene derivative having hydrogen atom at the 12-position of the present invention, or a light emitting layer comprising other conventional light emitting material may be laminated to the light emitting layer comprising the light emitting material of the present invention as long as the object of the present invention is not adversely affected.

The hole injecting and transporting layer is a layer which helps injection of holes into the light emitting layer and transports the holes to the light emitting region. The layer exhibits a great mobility of holes and, in general, has an ionization energy as small as 5.5 eV or smaller. For the hole injecting and transporting layer, a material which transports holes to the light emitting layer under an electric field of a smaller strength is preferable. A material which exhibits, for example, a mobility of holes of at least $10^{-4}$ cm$^2$/V·sec under application of an electric field of $10^4$ to $10^6$ V/cm is preferable. As the above material, a material can be selected as desired from materials which are conventionally used as the charge transporting material of holes in photoconductive materials and conventional materials which are used for the hole injecting layer in organic EL devices.

Examples include triazole derivatives (U.S. Pat. No. 3,112,197), oxadiazole derivatives (U.S. Pat. No. 3,189,447), imidazole derivatives (Japanese Patent Application Publication No. Showa 37 (1962)-16096), polyarylalkane derivatives (U.S. Pat. Nos. 3,615,402, 3,820,989 and 3,542,544; Japanese Patent Application Publication Nos. Showa 45 (1970)-555 and Showa 51 (1976)-10983; and Japanese Patent Application Laid-Open Nos. Showa 51 (1976)-93224, Showa 55 (1980)-17105, Showa 56 (1981)-4148, Showa 55 (1980)-108667, Showa 55 (1980)-156953 and Showa 56 (1981)-36656); pyrazoline derivatives and pyrazolone derivatives (U.S. Pat. Nos. 3,180,729 and 4,278,746; and Japanese Patent Application Laid-Open Nos. Showa 55 (1980)-88064, Showa 55 (1980)-88065, Showa 49 (1974)-105537, Showa 55 (1980)-51086, Showa 56 (1981)-80051, Showa 56 (1981)-88141, Showa 57 (1982)-45545, Showa 54 (1979)-112637 and Showa 55 (1980)-74546); phenylenediamine derivatives (U.S. Pat No. 3,615,404; Japanese Patent Application Publication Nos. Showa 51 (1976)-10105, Showa 46 (1971)-3712 and Showa 47 (1972)-25336; and Japanese Patent Application Laid-Open Nos. Showa 54 (1979)-53435, Showa 54 (1979)-110536 and Showa 54 (1979)-119925); arylamine derivatives (U.S. Pat. Nos. 3,567,450, 3,180,703, 3,240,597, 3,658,520, 4,232,103, 4,175,961 and 4,012,376; Japanese Patent Application Publication Nos. Showa 49 (1974)-35702 and Showa 39 (1964)-27577; Japanese Patent Application Laid-Open Nos. Showa 55 (1980)-144250, Showa 56 (1981)-119132 and Showa 56 (1981)-22437; and West German Patent No. 1,110,518); chalcone derivatives substituted with amino group (U.S. Pat. No. 3,526,501); oxazole derivatives (derivatives disclosed in U.S. Pat. No. 3,257,203); styrylanthracene derivatives (Japanese Patent Application Laid-Open Nos. Showa 56 (1981)-46234); fluorenone derivatives (Japanese Patent Application Laid-Open Nos. Showa 54 (1979)-110837); hydrazone derivatives (U.S. Pat. No. 3,717,462; and Japanese Patent Application Laid-Open Nos. Showa 54 (1979)-59143, Showa 55 (1980)-52063, Showa 55 (1980)-52064, Showa 55 (1980)-46760, Showa 55 (1980)-85495, Showa 57 (1982)-11350, Showa 57 (1982)-148749 and Heisei 2 (1990)-311591); stilbene derivatives (Japanese Patent Application Laid-Open Nos. Showa 61 (1986)-210363, Showa 61 (1986)-228451, Showa 61 (1986)-14642, Showa 61 (1986)-72255, Showa 62 (1987)-47646, Showa 62 (1987)-36674, Showa 62 (1987)-10652, Showa 62 (1987)-30255, Showa 60 (1985)-93455, Showa 60 (1985)-94462, Showa 60 (1985)-174749 and Showa 60 (1985)-175052); silazane derivatives (U.S. Pat. No. 4,950,950); polysilane-based compounds (Japanese Patent Application Laid-Open No. Heisei 2 (1990)-204996); aniline-based copolymers (Japanese Patent Application Laid-Open No. Heisei 2 (1990)-282263); and electrically conductive macromolecular oligomers (in particular, thiophene oligomers) disclosed in Japanese Patent Application Laid-Open No. Heisei 1 (1989)-211399.

Besides the above materials which can be used as the material for the hole injecting layer, porphyrin compounds (compounds disclosed in Japanese Patent Application Laid-Open No. Showa 63 (1988)-2956965); and aromatic tertiary amine compounds and styrylamine compounds (U.S. Pat. No. 4,127,412 and Japanese Patent Application Laid-Open Nos. Showa 53 (1978)-27033, Showa 54 (1979)-58445, Showa 54 (1979)-149634, Showa 54 (1979)-64299, Showa 55 (1980)-79450. Showa 55 (1980)-144250, Showa 56 (1981)-119132, Showa 61 (1986)-295558, Showa 61 (1986)-98353 and Showa 63 (1988)-295695) are preferable, and the aromatic tertiary amines are particularly preferable.

Further examples include compounds having two condensed aromatic rings in the molecule which are described in the U.S. Pat. No. 5,061,569 such as 4,4'-bis(N-(1-naphthyl)-N-phenylamino)-biphenyl (referred to as NPD, hereinafter) and a compound in which three triphenylamine units are bonded together in a star-burst shape, which is described in Japanese Patent Application Laid-Open No. Heisei 4 (1992)-308688, such as 4,4',4''-tris(N-(3-methylphenyl)-N-phenylamino)-triphenylamine (referred to as MTDATA, hereinafter).

Besides the above benzanthracene derivatives, inorganic compounds such as Si of the p-type and SiC of the p-type can also be used as the material for the hole injecting layer.

The hole injecting and transporting layer can be formed by preparing a thin film of the above compound in accordance with a conventional process such as the vacuum vapor deposition process, the spin coating process, the casting process and the LB process. The thickness of the hole injecting and transporting layer is not particularly limited. In general, the thickness is 5 nm to 5 μm.

The organic semiconductor layer is a layer helping injection of holes or electrons into the light emitting layer. As the organic semiconductor layer, a layer having a conductivity of $10^{-10}$ S/cm or greater is preferable. As the material for the organic semiconductor layer, oligomers containing thiophene can be used, and conductive oligomers such as oligomers containing arylamine and conductive dendrimers such as dendrimers containing arylamine, which are disclosed in Japanese Patent Application Laid-Open No. Heisei 8 (1996)-193191, can also be used.

The electron injecting and transporting layer is a layer which helps injection of electrons into the light emitting layer and transports the electrons to the light emitting region and exhibits a great mobility of electrons. The adhesion improving layer is an electron injecting layer comprising a material exhibiting improved adhesion with the cathode.

It is known that, in an organic EL device, emitted light is reflected at an electrode (the cathode in the present case), and the light obtained directly from the anode and the light obtained after reflection at the electrode interfere with each other. The thickness of the electron transporting layer is suitably selected in the range of several nm to several μm so that the interference is effectively utilized. When the thickness is great, it is preferable that the mobility of electrons is at least $10^{-5}$ cm²/Vs or greater under the application of an electric field of $10^4$ to $10^6$ V/cm so that the increase in the voltage is prevented.

As the material used for the electron injecting layer, metal complexes of 8-hydroxyquinoline and derivatives thereof and oxadiazole derivatives are preferable. Examples of the metal complexes of 8-hydroxyquinoline and the derivative thereof include metal chelated oxinoid compounds including chelate compounds of oxines (in general, 8-quinolinol or 8-hydroxyquinoline). For example, tris(8-quinolinol)-aluminum can be used as the electron injecting material.

Examples of the oxadiazole derivative include electron transfer compounds represented by the following general formulae:

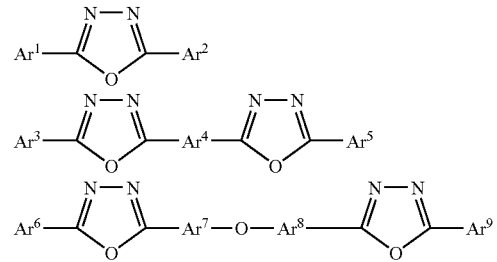

In the above formulae, $Ar^1$, $Ar^2$, $Ar^3$, $Ar^5$, $Ar^6$ and $Ar^9$ each represent a substituted or unsubstituted aryl group and may represent the same group or different groups. $Ar^4$, $Ar^7$ and $Ar^8$ each represent a substituted or unsubstituted arylene group and may represent the same group or different groups.

Examples of the aryl group include phenyl group, biphenyl group, anthranyl group, perylenyl group and pyrenyl group. Examples of the arylene group include phenylene group, naphthylene group, biphenylene group, anthranylene group, perylenylene group and pyrenylene group. Examples of the substituent include alkyl groups having 1 to 10 carbon atoms, alkoxy groups having 1 to 10 carbon atoms and cyano group. As the electron transfer compound, compounds which can form thin films are preferable.

Specific examples of the electron transfer compound include the following compounds:

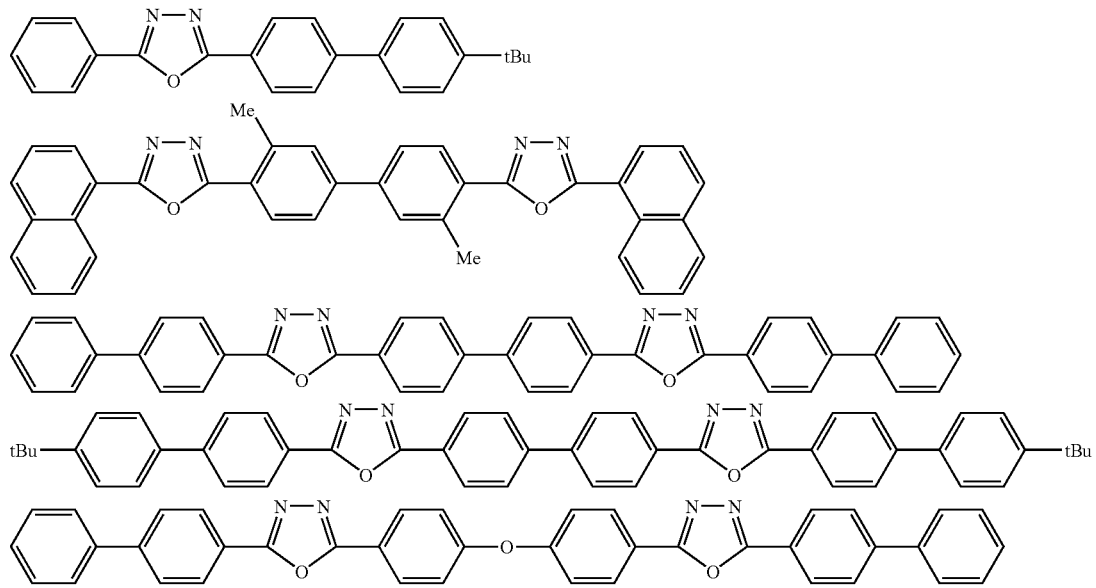

As the material which can be used for the electron injecting layer and the electron transporting layer, compounds represented by the following general formulae (E) to (J) can be used.

Heterocyclic derivatives having nitrogen atom represented by any one of general formulae (E) and (F):

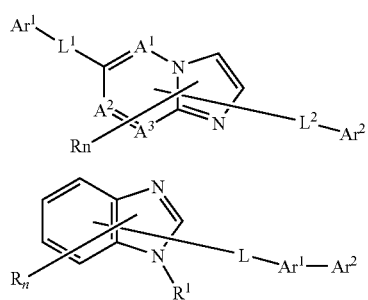

In general formulae (E) and (F), $A^1$ to $A^3$ each independently represent nitrogen atom or carbon atom.

$Ar^1$ represents a substituted or unsubstituted aryl group having 6 to 60 nuclear carbon atoms or a substituted or unsubstituted heteroaryl group having 3 to 60 nuclear carbon atoms; $Ar^2$ represents hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms, a substituted or unsubstituted alkoxy group having 1 to 20 carbon atoms or a divalent group derived from any of the above groups; and either one of $Ar^1$ and $Ar^2$ represents a substituted or unsubstituted condensed cyclic group having 10 to 60 nuclear carbon atoms or a substituted or unsubstituted monohetero condensed cyclic group having 3 to 60 nuclear carbon atoms.

$L^1$, $L^2$ and L each independently represent the single bond, a substituted or unsubstituted arylene group having 6 to 60 nuclear carbon atoms, a substituted or unsubstituted heteroarylene group having 3 to 60 nuclear carbon atoms or a substituted or unsubstituted fluorenylene group.

R represents hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms or a substituted or unsubstituted alkoxy group having 1 to 20 carbon atoms; n represents an integer of 0 to 5; and, when n represents an integer of 2 or greater, a plurality of atoms and groups represented by R may be the same with or different from each other, and a plurality of groups represented by R which are adjacent to each other may be bonded to each other to form an aliphatic ring of the carbon ring type or an aromatic ring of the carbon ring type.

Heterocyclic compounds having nitrogen atom represented by the following general formula (G):

In general formula (G), HAr represents a heterocyclic group having 3 to 40 carbon atoms and nitrogen atom which may have substituents, L represents the single bond or an arylene group having 6 to 60 carbon atoms which may have substituents, a heteroarylene group having 3 to 60 carbon atoms which may have substituents or a fluorenylene group which may have substituents, $Ar^1$ represents a divalent aromatic hydrocarbon group having 6 to 60 carbon atoms which may have substituents, and $Ar^2$ represents an aryl group having 6 to 60 carbon atoms which may have substituents or a heteroaryl group having 3 to 60 carbon atoms which may have substituents.

Silacyclopentadiene derivatives represented by the following general formula (H):

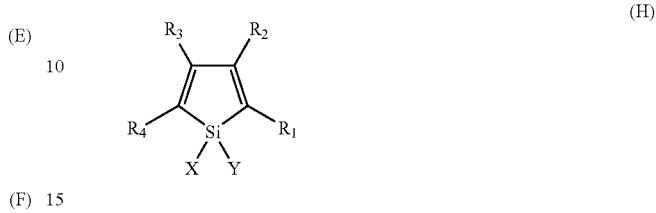

In general formula (H), X and Y each independently represent a saturated or unsaturated hydrocarbon group having 1 to 6 carbon atoms, an alkoxy group, an alkenyloxy group, an alkynyloxy group, hydroxy group, a substituted or unsubstituted aryl group, a substituted or unsubstituted heterocyclic group or a saturated or unsaturated cyclic group formed by bonding of the above groups represented by X and Y; and $R_1$ to $R_4$ each independently represent hydrogen atom, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, sulfinyl group, sulfonyl group, sulfanyl group, silyl group, carbamoyl group, an aryl group, a heterocyclic group, an alkenyl group, an alkynyl group, nitro group, formyl group, nitroso group, formyloxy group, isocyano group, cyanate group, isocyanate group, thiocyanate group, isothiocyanate group, a cyano group or, when the groups are adjacent to each other, a structure formed by condensation of substituted or unsubstituted rings.

Borane derivatives represented by the following general formula (I):

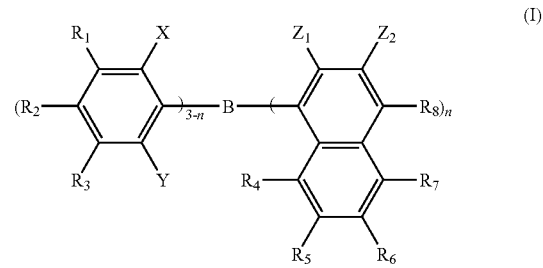

In general formula (I), $R_1$ to $R_8$ and $Z_2$ each independently represent hydrogen atom, a saturated or unsaturated hydrocarbon group, an aromatic hydrocarbon group, a heterocyclic group, a substituted amino group, a substituted boryl group, an alkoxy group or an aryloxy group; X, Y and $Z_1$ each independently represent a saturated or unsaturated hydrocarbon group, an aromatic hydrocarbon group, a heterocyclic group, a substituted amino group, an alkoxy group or an aryloxy group, and substituents to the groups represented by $Z_1$ and $Z_2$ may be bonded to each other to form a condensed ring; n represents an integer of 1 to 3 and, when n represents an integer of 2 or greater, a plurality of $Z_1$ may represent different groups; and the case where n represents 1, X, Y and R₂ each represent methyl group and R₈ represents hydrogen atom or a substituted boryl group and the case where n represents 3 and Z₁ represents methyl group are excluded.

Compounds represented by general formula (J):

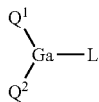

(J)

In general formula (J), Q₁ and Q₂ each independently represent a ligand represented by the general formula (K) described below; and L represents a halogen atom, a substituted or unsubstituted alkyl group, a substituted or unsubstituted cycloalkyl group, a substituted or unsubstituted aryl group, a substituted or unsubstituted heterocyclic group or a ligand represented by —OR¹ (R¹ representing hydrogen atom, a substituted or unsubstituted alkyl group, a substituted or unsubstituted cycloalkyl group, a substituted or unsubstituted aryl group or a substituted or unsubstituted heterocyclic group) or —O—Ga-Q³(Q⁴) (Q³ and Q⁴ being same as defined for Q¹ and Q²).

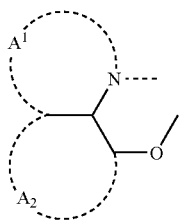

(K)

(rings A¹ and A² each representing six-membered aryl cyclic structure which may have substituents and are condensed with each other), The above metal complex compound strongly exhibits the property as the n-type semiconductor and a great ability of electron injection, and the energy of formation of the complex compound is small. Therefore, the bonding between the metal and the ligand in the formed metal complex compound is strong, and the quantum efficiency of fluorescence as the light emitting material is great.

Examples of the substituent to rings represented by A1 and A2 forming the ligand represented by general formula (K) include halogen atoms such as chlorine atom, bromine atom, iodine atom and fluorine atom; substituted and unsubstituted alkyl groups such as methyl group, ethyl group, propyl group, butyl group, s-butyl group, t-butyl group, pentyl group, hexyl group, heptyl group, octyl group, stearyl group and trichloromethyl group; substituted and unsubstituted aryl groups such as phenyl group, naphthyl group, 3-methylphenyl group, 3-methoxyphenyl group, 3-fluorophenyl group, 3-trichloromethylphenyl group, 3-trifluoro-methylphenyl group and 3-nitrophenyl group; substituted and unsubstituted alkoxy groups such as methoxy group, n-butoxy group, t-butoxy group, trichloromethoxy group, trifluoroethoxy group, pentafluoropropoxy group, 2,2,3,3-tetrafluoropropoxy group, 1,1,1,3,3,3-hexafluoro-2-propoxy group and 6-(perfluoroethyl)hexyloxy group; substituted and unsubstituted aryloxy groups such as phenoxy group, p-nitrophenoxy group, p-t-butylphenoxy group, 3-fluorophenoxy group, pentafluorophenoxy group and 3-trifluoromethylphenoxy group; substituted and unsubstituted alkylthio groups such as methylthio group, ethylthio group, t-butylthio group, hexylthio group, octylthio group and trifluoromethylthio group; substituted and unsubstituted arylthio groups such as phenylthio group, p-nitrophenylthio group, p-t-butylphenylthio group, 3-fluorophenylthio group, pentafluorophenylthio group and 3-trifluoromethylphenylthio group; cyano group; nitro group; amino group; mono- and disubstituted amino groups such as methylamino group, dimethylamino group, ethylamino group, diethylamino group, dipropyl-amino group, dibutylamiono group and diphenylamino group; acylamino groups such as bis(acetoxymethyl)amino group, bis(acetoxyethyl)amino group, bis(acetoxypropyl)amino group and bis(acetoxybutyl)amino group; hydroxy group; siloxy group; acyl group; carbamoyl groups such as methylcarbamoyl group, dimethylcarbamoyl group, ethylcarbamoyl group, diethylcarbamoyl group, propylcarbamoyl group, butylcarbamoyl group and phenylcarbamoyl group; carboxylic acid group; sulfonic acid group; imide group; cycloalkyl groups such as cyclopentane group and cyclohexyl group; aryl groups such as phenyl group, naphthyl group, biphenyl group, anthranyl group, phenanthryl group, fluorenyl group and pyrenyl group; and heterocyclic groups such as pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triatinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, benzimidazolyl group and planyl group. The above substituents may be bonded to each other to form a six-membered aryl group or heterocyclic group.

A device comprising a reducing dopant in the interfacial region between a region transporting electrons or the cathode and the organic layer is preferable as an embodiment of the organic EL device of the present invention. The reducing dopant is defined as a substance which can reduce a compound having the electron transporting property. Various compounds can be used as the reducing dopant as long as the compounds have the specific reductive property. For example, at least one substance selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals can be advantageously used.

Preferable examples of the reducing dopant include substances having a work function of 2.9 eV or smaller, specific examples of which include at least one alkali metal selected from the group consisting of Na (the work function: 2.36 eV), K (the work function: 2.28 eV), Rb (the work function: 2.16 eV) and Cs (the work function: 1.95 eV) and at least one alkaline earth metal selected from the group consisting of Ca (the work function: 2.9 eV), Sr (the work function: 2.0 to 2.5 eV) and Ba (the work function: 2.52 eV). Among the above substances, at least one alkali metal selected from the group consisting of K, Rb and Cs is more preferable, Rb and Cs are still more preferable, and Cs is most preferable as the reducing dopant. These alkali metals have great reducing ability, and the luminance of the emitted light and the life of the organic EL device can be increased by addition of a relatively small amount of the alkali metal into the electron injecting zone. As the reducing dopant having a work function of 2.9 eV or smaller, combinations of two or more alkali metals are also preferable. Combinations having Cs such as the combinations of Cs and Na, Cs and K, Cs and Rb and Cs, Na and K are more preferable. The reducing ability can be efficiently exhibited by the combination having Cs. The luminance of emitted light and the life of the organic EL device can be increased by adding the combination having Cs into the electron injecting zone.

The organic EL device of the present invention may further comprise an electron injecting layer which is constituted with an insulating material or a semiconductor and disposed between the cathode and the organic layer. By the electron injecting layer, leak of electric current can be effectively prevented, and the electron injecting property can be improved. As the insulating material, at least one metal compound selected from the group consisting of alkali metal chalcogenides, alkaline earth metal chalcogenides, halides of alkali metals and halides of alkaline earth metals is preferable. It is preferable that the electron injecting layer is constituted with the above substance such as the alkali metal chalcogenide since the electron injecting property can be further improved. Preferable examples of the alkali metal chalcogenide include $Li_2O$, $K_2O$, $Na_2S$, $Na_2Se$ and NaO. Preferable examples of the alkaline earth metal chalcogenide include CaO, BaO, SrO, BeO, BaS and CaSe. Preferable examples of the halide of an alkali metal include LiF, NaF, KF, LiCl, KCl and NaCl. Preferable examples of the halide of an alkaline earth metal include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides of at least one metal selected from Ba, Ca, Sr, Yb, Al, Ga, In, Li, Na, Cd, Mg, Si, Ta, Sb and Zn used singly or in combination of two or more. It is preferable that the inorganic compound constituting the electron transporting layer forms a crystallite or amorphous insulating thin film. When the electron injecting layer is constituted with the insulating thin film described above, a more uniform thin film can be formed, and defects of pixels such as dark spots can be decreased. Examples of the inorganic compound include alkali metal chalcogenides, alkaline earth metal chalcogenides, halides of alkali metals and halides of alkaline earth metals which are described above.

For the cathode, a material such as a metal, an alloy, a conductive compound or a mixture of these materials which has a small work function (4 eV or smaller) is used as the electrode material. Examples of the electrode material include sodium, sodium-potassium alloys, magnesium, lithium, magnesium-silver alloys, aluminum/aluminum oxide, $Al/Li_2O$, $Al/LiO_2$, Al/LiF, aluminum-lithium alloys, indium and rare earth metals.

The cathode can be prepared by forming a thin film of the electrode material described above in accordance with a process such as the vapor deposition process and the sputtering process.

When the light emitted from the light emitting layer is obtained through the cathode, it is preferable that the cathode has a transmittance of the emitted light greater than 10%. It is also preferable that the sheet resistivity of the cathode is several hundred $\Omega/\square$ or smaller. The thickness of the cathode is, in general, selected in the range of 10 nm to 1 μm and preferably in the range of 50 to 200 nm.

Defects in pixels tend to be formed in organic EL device due to leak and short circuit since an electric field is applied to ultra-thin films. To prevent the formation of the defects, a layer of a thin film having an insulating property may be inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be used.

To prepare the organic EL device of the present invention, for example, the anode, the light emitting layer and, where necessary, the hole injecting layer and the electron injecting layer are formed in accordance with the above process using the above materials, and the cathode is formed in the last step. The organic EL device may be prepared by forming the above layers in the order reverse to that described above, i.e., the cathode being formed in the first step and the anode in the last step.

An embodiment of the process for preparing an organic EL device having a construction in which an anode, a hole injecting layer, a light emitting layer, an electron injecting layer and a cathode are disposed successively on a substrate transmitting light will be described in the following.

On a suitable substrate which transmits light, a thin film made of a material for the anode is formed in accordance with the vapor deposition process or the sputtering process so that the thickness of the formed thin film is 1 μm or smaller and preferably in the range of 10 to 200 nm. The formed thin film is used as the anode. Then, a hole injecting layer is formed on the anode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions are suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C. and the thickness of the film: 5 nm to 5 μm; although the conditions of the vacuum vapor deposition are different depending on the used compound (the material for the hole injecting layer) and the crystal structure and the recombination structure of the hole injecting layer to be formed.

Then, the light emitting layer is formed on the hole injecting layer formed above. The light emitting layer can be obtained, using the light emitting material of the present invention, by forming a thin film of the light emitting material in accordance with the vacuum vapor deposition process, the sputtering process, the spin coating process or the casting process. The vacuum vapor deposition process is preferable since a uniform film can be easily obtained and the possibility of formation of pin holes is small. When the light emitting layer is formed in accordance with the vacuum vapor deposition process, in general, the conditions of the vacuum vapor deposition process can be selected in the same ranges as those described for the vacuum vapor deposition to form the hole injecting layer although the conditions are different depending on the used compound. It is preferable that the thickness is in the range of 10 to 40 nm.

The electron injecting layer is formed on the light emitting layer formed above. Similarly to the hole injecting layer and the light emitting layer, it is preferable that the electron injecting layer is formed in accordance with the vacuum vapor deposition process since a uniform film must be obtained. The conditions of the vacuum vapor deposition can be selected in the same ranges as those described for the vacuum vapor deposition to form the hole injecting layer and the light emitting layer.

The cathode is formed on the electron injecting layer formed above in the last step, and the organic EL device can be obtained. The cathode is made of a metal and can be formed in accordance with the vacuum vapor deposition process or the sputtering process. It is preferable that the vacuum vapor deposition process is used in order to prevent formation of damages on the lower organic layers during the formation of the film.

In the above preparation of the organic EL device, it is preferable that the above layers from the anode to the cathode are formed successively while the preparation system is kept in a vacuum after being evacuated once.

The process for forming the layers in the organic EL device of the present invention is not particularly limited. A conventional process such as the vacuum vapor deposition process and the spin coating process can be used. The organic thin film layer which is used in the organic EL device of the present invention and comprises the compound represented by general formula (1) described above can be formed in accordance with a conventional process such as the vacuum vapor deposition process and the molecular beam epitaxy process (the MBE process) or, using a solution prepared by dissolving the compounds into a solvent, in accordance with a coating process such as the dipping process, the spin coating process, the casting process, the bar coating process and the roll coating process.

The thickness of each layer in the organic thin film layer in the organic EL device of the present invention is not particularly limited. A thickness in the range of several nanometers to 1 μm is preferable so that defects such as pin holes are decreased and the efficiency can be improved.

When a direct voltage is applied to the organic EL device, emission of light can be observed under application of a voltage of 5 to 40 V in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be used.

EXAMPLES

The present invention will be described more specifically with reference to examples in the following. However, the present invention is not limited to the examples.

Synthesis Example 1 (Synthesis of BAN-2)

Into 300 ml of DMF, N,N-dimethylformamide, 40 g of commercial benzanthracene was dispersed, and 35.6 g of NBS, bromosuccinimide, was added to the resultant suspension at the room temperature. After the resultant mixture was stirred for 3.5 hours, 600 ml of water was added, and the formed crystals were separated by filtration and washed with methanol. The obtained crude crystals were purified using a silica gel column with toluene and filtered with hexane, and 49.3 g of 7-bromobenzanthracene was obtained as cream crystals (the yield: 91%).

Into 200 ml of dehydrated THF, tetrahydrofuran, 20 g of 7-bromobenzanthracene obtained above was dissolved, and the obtained solution was cooled at −62° C. To the cooled solution, 50 ml of a 1.6 M hexane solution of normal-butyl-lithium was added dropwise, and the resultant mixture was stirred for 30 minutes. The temperature was raised to −5° C. and then lowered to −64° C. To the cooled fluid, a THF solution of 22.4 g of trimethyl borate was added dropwise. After one night, the reaction fluid was adjusted at the acidic condition with a dilute hydrochloric acid, treated by extraction with toluene and washed with water and a saturated aqueous solution of sodium chloride, and the organic layer was dried with anhydrous sodium sulfate. After the solvent was removed by distillation, the obtained residue was crystallized from toluene/hexane, and 14 g of 7-benzanthraceneboronic acid was obtained as cream crystals (the yield: 79%).

Under the atmosphere of argon, 6.73 g of 3-(naphthalen-2-yl)-(6-bromonaphthalen-2-yl)benzene synthesized in accordance with a conventional process and 4.92 g of 7-benzanthraceneboronic acid were dispersed into 80 ml of toluene and 80 ml of DME 1,1-dimethoxyethane, and 25 ml of a 2M aqueous solution of sodium carbonate was added to the resultant dispersion. To the obtained mixture, 0.57 g of tetrakis-triphenyl-phosphinepalladium was added, and the resultant mixture was heated under the refluxing condition for 7 hours. After one night, the formed precipitates were removed by filtration, and the mother liquor was washed with water and a saturated aqueous solution of sodium chloride. The organic layer was dried with anhydrous sodium sulfate, and the solvent was removed by distillation. The obtained residue was crystallized from acetone, and 4.7 g of the object compound (BAN-2) was obtained as grayish white crystals (the yield: 51%). When the obtained compound was examined in accordance with the field desorption mass spectroscopy (FD-MS), it was found that m/z=556, which agreed with $C_{44}H_{28}$=556, and the above compound was identified to be BAN-2.

Synthesis Example 2 (Synthesis of BAN-3)

Under the atmosphere of argon, 4.4 g of 3-(naphthalen-2-yl)phenyl-boronic acid synthesized in accordance with a conventional process and 5 g of 7-bromobenzanthracene were dispersed into 60 ml of toluene, and 26 ml of a 2M aqueous solution of sodium carbonate was added to the resultant dispersion. To the obtained mixture, 0.57 g of tetrakis-triphenylphosphinepalladium was added, and the resultant mixture was heated under the refluxing condition for 7 hours. After one night, the formed precipitates were removed by filtration, and the mother liquor was washed with water and a saturated aqueous solution of sodium chloride. The organic layer was dried with anhydrous sodium sulfate, and the solvent was removed by distillation. The obtained residue was crystallized from toluene/hexane, and 4.3 g of the object compound (BAN-3) was obtained as grayish white crystals (the yield: 61%). When the obtained compound was examined in accordance with the field desorption mass spectroscopy (FD-MS), it was found that m/z=430, which agreed with $C_{34}H_{22}$=430, and the above compound was identified to be BAN-3.

Synthesis Example 3 (Synthesis of BAN-17)

Under the atmosphere of argon, 2.65 g of p-dibromobenzene and 6.7 g of 7-benzanthraceneboronic acid were dispersed into 80 ml of toluene and 80 ml of DME, and 40 ml of a 2M aqueous solution of sodium carbonate was added to the resultant dispersion. To the obtained mixture, 0.78 g of tetrakistriphenylphosphinepalladium was added, and the resultant mixture was heated under the refluxing condition for 8 hours. After one night, the formed precipitates were separated by filtration. The obtained crystals were washed with water, methanol and heated toluene, and 4.6 g of the object compound (BAN-17) was obtained as grayish white crystals (the yield: 78%). When the obtained compound was examined in accordance with the field desorption mass spectroscopy (FD-MS), it was found that m/z=530, which agreed with $C_{42}H_{26}$=530, and the above compound was identified to be BAN-17.

Synthesis Example 4 (Synthesis of BAN-18)

Under the atmosphere of argon, 4 g of 2,6-dibromonaphthalene and 8.4 g of 7-benzanthraceneboronic acid were dispersed into 100 ml of toluene and 100 ml of DME, and 46 ml of a 2M aqueous solution of sodium carbonate was added to the resultant dispersion. To the obtained mixture, 0.97 g of tetrakistriphenylphosphinepalladium was added, and the resultant mixture was heated under the refluxing condition for 8 hours. After one night, the formed precipitates were separated by filtration. The obtained crystals were washed with water, methanol and heated toluene, and 6.7 g of the object compound (BAN-18) was obtained as grayish white crystals (the yield: 82%). When the obtained compound was examined in accordance with the field desorption mass spectroscopy (FD-MS), it was found that m/z=580, which agreed with $C_{46}H_{28}$=580, and the above compound was identified to be BAN-18.

Synthesis Example 5 (Synthesis of BAN-22)

Under the atmosphere of argon, 4 g of 2,7-dibromo-9,9-dimethyl-9H-fluorene and 6.8 g of 7-benzanthraceneboronic acid were dispersed into 100 ml of toluene and 100 ml of DME, and 38 ml of a 2M aqueous solution of sodium carbonate was added to the resultant dispersion. To the obtained mixture, 0.79 g of tetrakistriphenylphosphinepalladium was added, and the resultant mixture was heated under the refluxing condition for 8 hours. After one night, the formed precipitates were separated by filtration. The obtained crystals were washed with water, methanol and heated toluene, and 5.0 g of the object compound (BAN-22) was obtained as grayish white crystals (the yield: 68%). When the obtained compound was examined in accordance with the field desorption mass spectroscopy (FD-MS), it was found that m/z=646, which agreed with $C_{51}H_{34}$=646, and the above compound was identified to be BAN-22.

Synthesis Example 6 (Synthesis of BAN-25)

Under the atmosphere of argon, 2.8 g of 1,3,5-tribromobenzene and 8.0 g of 7-benzanthraceneboronic acid were dispersed into 100 ml of toluene and 100 ml of DME, and 45 ml of a 2M aqueous solution of sodium carbonate was added to the resultant dispersion. To the obtained mixture, 0.72 g of tetrakistriphenylphosphinepalladium was added, and the resultant mixture was heated under the refluxing condition for 8 hours. After one night, the formed precipitates were separated by filtration. The obtained crystals were washed with water, methanol and heated toluene, and 4.5 g of the object compound (BAN-25) was obtained as grayish white crystals (the yield: 66%). When the obtained compound was examined in accordance with the field desorption mass spectroscopy (FD-MS), it was found that m/z=756, which agreed with $C_{60}H_{36}$=756, and the above compound was identified to be BAN-25.

Synthesis Example 7 (Synthesis of BAN-36)

Under the atmosphere of argon, 6.1 g of 3-(9-(naphthalen-2-yl)-anthracen-10-yl)phenylboronic acid synthesized in accordance with a conventional process and 4.0 g of 7-bromobenzanthracene were dispersed into 80 ml of toluene and 80 ml of DME, and 25 ml of a 2M aqueous solution of sodium carbonate was added to the resultant dispersion. To the obtained mixture, 0.45 g of tetrakistriphenylphosphine-palladium was added, and the resultant mixture was heated under the refluxing condition for 7 hours. After one night, the formed precipitates were removed by filtration, and the mother liquor was washed with water and a saturated aqueous solution of sodium chloride. The organic layer was dried with anhydrous sodium sulfate, and the solvent was removed by distillation. The obtained residue was crystallized from toluene/hexane, and 6.24 g of the object compound (BAN-36) was obtained as cream crystals (the yield: 78%). When the obtained compound was examined in accordance with the field desorption mass spectroscopy (FD-MS), it was found that m/z=606, which agreed with $C_{48}H_{30}$=606, and the above compound was identified to be BAN-36.

Example 1 (Evaluation of BAN-3)

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes. The cleaned glass substrate having the transparent electrode was attached to a substrate holder of a vacuum vapor deposition apparatus. On the surface of the cleaned substrate at the side having the transparent electrode, a film of N,N'-bis(N,N'-diphenyl-4-aminophenyl)-N,N-diphenyl-4,4'-diamino-1,1'-biphenyl (referred to as a TPD232 film, hereinafter) having a thickness of 60 nm was formed in a manner such that the formed film covered the transparent electrode. The formed TPD232 film worked as the hole injecting layer. On the formed TPD232 film, a layer of N,N,N',N'-tetra(4-biphenyl)diaminobiphenylene (referred to as a TBDB layer, hereinafter) having a thickness of 20 nm was formed. The formed TBDB film worked as the hole transporting layer. On the formed TBDB film, BAN-3 was vapor deposited to form a film having a thickness of 40 nm. At the same time, as the light emitting molecule, an amine compound BD1 shown below was vapor deposited in an amount such that the ratio of the amounts by weight of BAN-3 to BD1 were 40:2. The formed film worked as the light emitting layer. On the formed film, a film of Alq shown in the following having a thickness of 10 nm was formed. This film worked as the electron injecting layer. On the film formed above, Li (the source of Li: manufactured by SAES GETTERS Company) as the reducing dopant and Alq were binary vapor deposited, and an Alq:Li film (the thickness: 10 nm) was formed as the electron injecting layer (the cathode). On the formed Alq:Li film, Al metal was vapor deposited to form the metal cathode, and an organic EL device was prepared. The obtained organic EL device was examined by passing electric current. Blue light having a luminance of emitted light of 768 cd/m² was emitted under a voltage of 6.9 V and a current density of 10 mA/cm². The initial luminance was set at 1,000 cd/m², and the half life of the obtained organic EL device was measured. The result is shown in Table 1.

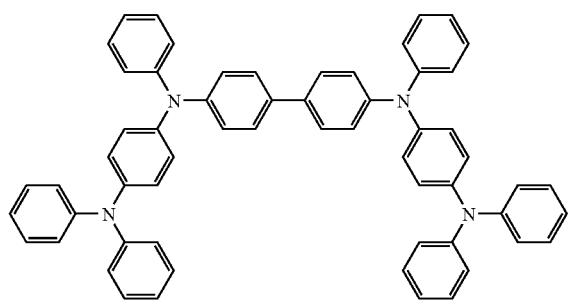

TPD232

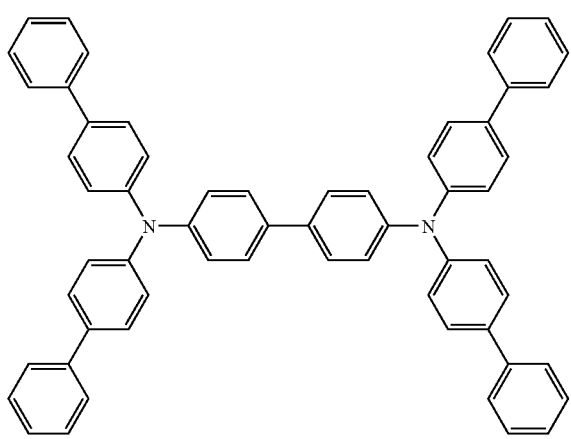

TBDB

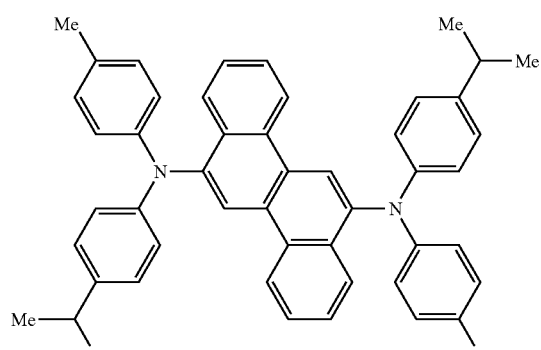

BD1

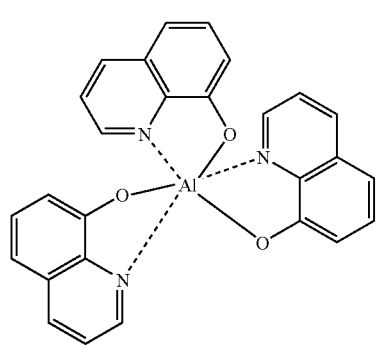

Alq

Examples 2 to 5 (Preparation of organic EL devices)

Organic EL devices were prepared in accordance with the same procedures as those conducted in Example 1 except that the compounds shown in Table 1 were used as the material for the light emitting layer in place of BAN-3. The half life of the obtained devices was measured in accordance with the same procedure as that conducted in Example 1. The results are shown in Table 1.

Example 6

An organic EL device was prepared in accordance with the same procedures as those conducted in Example 1 except that an amine compound BD2 was used as the material for the light emitting layer in place of the amine compound BD1. The half life of the obtained device was measured in accordance with the same procedure as that conducted in Example 1. The result is shown in Table 1.

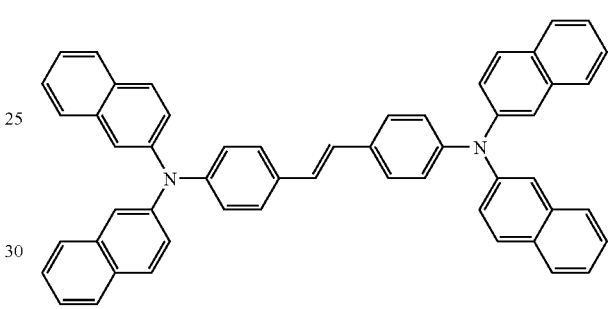

BD2

Example 7

An organic EL device was prepared in accordance with the same procedures as those conducted in Example 1 except that an amine compound BD3 was used as the material for the light emitting layer in place of the amine compound BD1. The half life of the obtained device was measured in accordance with the same procedure as that conducted in Example 1. The result is shown in Table 1.

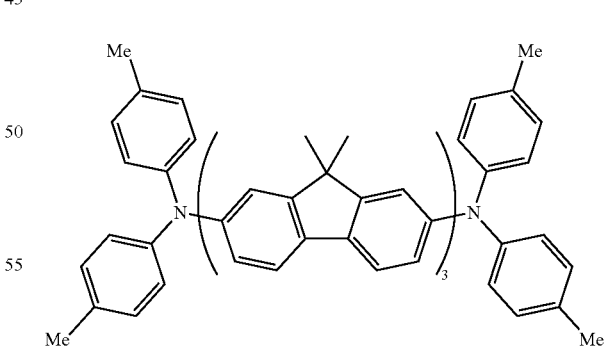

BD3

Comparative Example 1

An organic EL device was prepared in accordance with the same procedures as those conducted in Example 1 except that ban-1 was used as the material for the light emitting layer in place of BAN-3.

The initial luminance was set at 1,000 cd/m², and the half life of the obtained organic EL device was measured. The result is shown in Table 1.

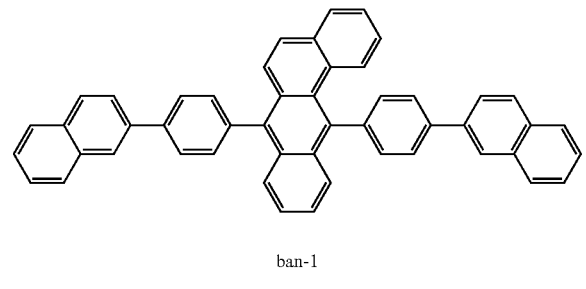

ban-1

Comparative Example 2

An organic EL device was prepared in accordance with the same procedures as those conducted in Example 1 except that ban-2 was used as the material for the light emitting layer in place of BAN-3.

The initial luminance was set at 1,000 cd/m², and the half life of the obtained organic EL device was measured. The result is shown in Table 1.

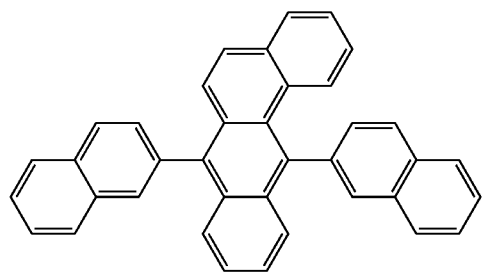

ban-2

Comparative Example 3

An organic EL device was prepared in accordance with the same procedures as those conducted in Example 1 except that ban-3 was used as the material for the light emitting layer in place of BAN-3.

The initial luminance was set at 1,000 cd/m², and the half life of the obtained organic EL device was measured. The result is shown in Table 1.

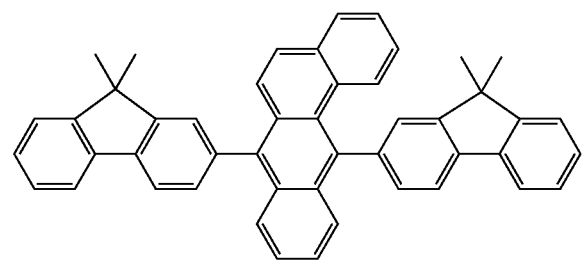

ban-3

TABLE 1

| | Compound used in light emitting layer | Half life (hour) | Chromaticity | |
|---|---|---|---|---|
| | | | CIEx | CIEy |
| Example 1 | BAN-3/BD-1 | 5,200 | 0.14 | 0.20 |
| Example 2 | BAN-17/BD-1 | 5,100 | 0.15 | 0.20 |
| Example 3 | BAN-18/BD-1 | 4,800 | 0.16 | 0.21 |
| Example 4 | BAN-22/BD-1 | 4,000 | 0.14 | 0.20 |
| Example 5 | BAN-25/BD-1 | 3,900 | 0.15 | 0.21 |
| Example 6 | BAN-3/BD-2 | 4,500 | 0.14 | 0.19 |
| Example 7 | BAN-3/BD-3 | 3,900 | 0.15 | 0.19 |
| Comparative Example 1 | ban-1/BD-1 | 3,000 | 0.20 | 0.29 |
| Comparative Example 2 | ban-2/BD-1 | 2,800 | 0.21 | 0.35 |
| Comparative Example 3 | ban-3/BD-1 | 2,000 | 0.20 | 0.31 |

As shown in Table 1, the benzanthracene derivative having hydrogen atom at the 12-position of the present invention provided more excellent chromaticities and longer lives than those provided by the conventional technology.

INDUSTRIAL APPLICABILITY

As described specifically in the above, the benzanthracene derivative having hydrogen atom at the 12-position of the present invention provides a more excellent chromaticity and a longer life.

The invention claimed is:

1. An organic electroluminescence device comprising a cathode, an anode and an organic thin film layer which comprises one layer or a plurality of layers comprising at least a light emitting layer and is disposed between the cathode and the anode, wherein the organic thin film layer comprises at least one benzanthracene derivative having hydrogen atom at a 12-position which is represented by formula (1):

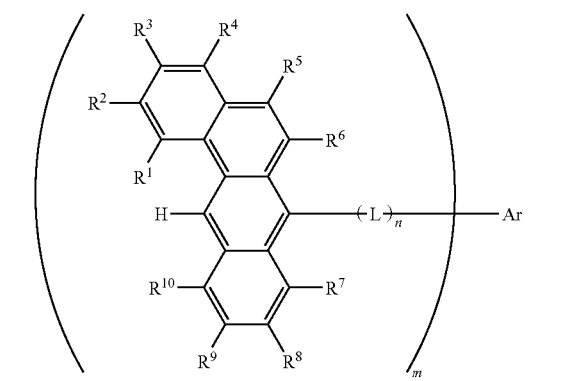

(1)

wherein
$R^1$ to $R^{10}$ each independently represent hydrogen atom, a substituted or unsubstituted aromatic hydrocarbon cyclic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted cycloalkyl group having 3 to 50 nuclear carbon atoms, a substituted or unsubstituted alkoxy group having 1 to 50 carbon atoms, a substituted or unsubstituted aralkyl group having 6 to 50 nuclear carbon atoms, a substituted or unsubstituted aryloxy group having 5 to 50 nuclear carbon atoms, a substituted or unsubstituted arylthio group having 5 to 50 nuclear carbon atoms, a substituted or unsubstituted alkoxycarbonyl group having 1 to 50 carbon atoms, a substituted or unsubstituted silyl group 1 to 50 carbon atoms, carboxy group, a halogen atom, cyano group, nitro group or hydroxy group;

L represents a linking group, which is a single bond, a substituted or unsubstituted divalent aromatic hydrocarbon cyclic group having 6 to 50 nuclear carbon atoms, a substituted or unsubstituted divalent aromatic heterocyclic group having 5 to 50 nuclear atoms, a substituted or unsubstituted fluorenylene group or a substituted or unsubstituted carbazolylene group;

n represents an integer of 1 to 4 and, when n represents an integer of 2 or greater, a plurality of linking groups represented by L may be same with or different from each other;

Ar represents a single bond, hydrogen atom, a substituted or unsubstituted aromatic hydrocarbon cyclic group having 6 to 50 nuclear carbon atoms, a substituted or unsubstituted aromatic heterocyclic group having 5 to 50 nuclear atoms, fluorenyl group or carbazolyl group; and m represents an integer of 1 to 4 and, when m represents an integer of 2 or greater, a plurality of atoms and groups represented by $R^1$ to $R^{10}$ and L may be same with or different from each other, the light emitting layer comprises a styrylamine compound represented by formula (A):

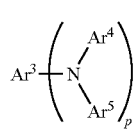

(A)

wherein $Ar^3$ represents a group selected from phenyl group, biphenyl group, terphenyl group, stilbene group and distyrylaryl groups, $Ar^4$ and $Ar^5$ each represent hydrogen atom or an aromatic hydrocarbon group having 6 to 20 carbon atoms, the groups represented by $Ar^3$, $Ar^4$ and $Ar^5$ may be substituted, p represents an integer of 1 to 4, or the light emitting layer comprises an arylamine compound represented by formula (B)

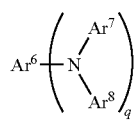

(B)

wherein $Ar^6$ to $Ar^8$ each represent a substituted or unsubstituted aryl group having 5 to 40 nuclear carbon atoms, and q represents an integer of 1 to 4.

2. The organic electroluminescence device according to according to claim 1, wherein the compound represented by formula (1) is a compound represented by formula (2):

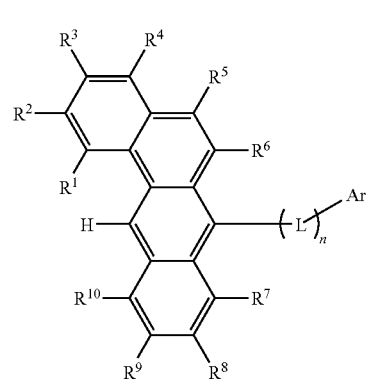

(2)

wherein $R^1$ to $R^{10}$, L and n are each independently same as defined in general formula (1), and Ar represents hydrogen atom, a substituted or unsubstituted aromatic hydrocarbon cyclic group having 6 to 50 nuclear carbon atoms, a substituted or unsubstituted aromatic heterocyclic group having 5 to 50 nuclear atoms, fluorenyl group or carbazolyl group.

3. The organic electroluminescence device according to according to claim 1, wherein the compound represented by formula (1) is a compound represented by formula (3):

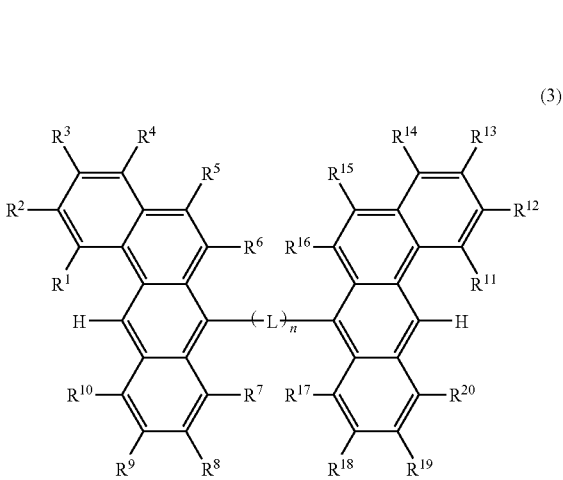

(3)

wherein $R^1$ to $R^{20}$ are each independently same as defined for $R^1$ to $R^{10}$ in general formula (1), and L and n are each independently same as defined in general formula (1).

4. The organic electroluminescence device according to according to claim 1, wherein the compound represented by formula (1) is a compound represented by formula (4):

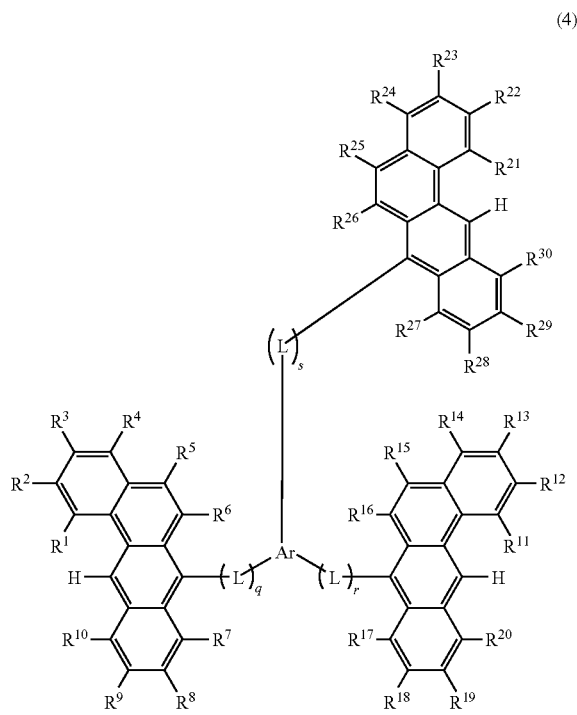 (4)

wherein $R^1$ to $R^{30}$ are each independently same as defined for $R^1$ to $R^{10}$ in general formula (1), L is same as defined in general formula (1), q, r and s are each same as defined for n in general formula (1), and Ar represents a substituted or unsubstituted aromatic hydrocarbon cyclic group having 6 to 50 nuclear carbon atoms, a substituted or unsubstituted aromatic heterocyclic group having 5 to 50 nuclear atoms, fluorenyl group or carbazolyl group.

5. The organic electroluminescence device according to according to claim 1, wherein the light emitting layer comprises a benzanthracene derivative having hydrogen atom at a 12-position described in formula (1).

6. The organic electroluminescence device according to according to claim 1, wherein the light emitting layer comprises the arylamine compound represented by formula (B).

7. The organic electroluminescence device according to according to claim 1, wherein the light emitting layer comprises the styrylamine compound represented by formula (A).

8. The organic electroluminescence device according to according to claim 1, wherein the light emitting layer comprises the styrylamine compound represented by formula (A) and at least one of the groups represented by $Ar^4$ and $Ar^5$ is substituted with styryl group.

9. The organic electroluminescence device according to according to claim 1, wherein the light emitting layer comprises the styrylamine compound represented by formula (A) and at least one of the groups represented by $Ar^3$ to $Ar^5$ has a substituted or unsubstituted styryl group.

\* \* \* \* \*